United States Patent
Nivaggioli et al.

(10) Patent No.: US 6,326,028 B1
(45) Date of Patent: Dec. 4, 2001

(54) ALGINATE AND GELLAN GUM AS TABLET COATING

(75) Inventors: Thierry Nivaggioli, San Francisco; George Colegrove, San Diego, both of CA (US); John Flanagan, Neshanic Station, NJ (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/183,238

(22) Filed: Oct. 30, 1998

Related U.S. Application Data

(60) Provisional application No. 60/064,454, filed on Oct. 31, 1997.

(51) Int. Cl.[7] ............... A61K 9/28; A61K 9/34; A61K 9/36
(52) U.S. Cl. .......... 424/481; 424/474; 424/475; 424/479; 514/777; 514/779; 514/782
(58) Field of Search .................. 424/474, 475, 424/479, 481

(56) References Cited

U.S. PATENT DOCUMENTS

| | | | | |
|---|---|---|---|---|
| 4,857,337 | * | 8/1989 | Miller et al. | 424/480 |
| 5,545,410 | * | 8/1996 | Fox et al. | 424/439 |
| 5,648,097 | * | 7/1997 | Nuwayser | 424/489 |
| 5,786,188 | * | 7/1998 | Lamar et al. | 435/177 |
| 5,879,712 | * | 3/1999 | Bomberger et al. | 424/489 |
| 5,977,023 | * | 11/1999 | Inoue et al. | 504/116 |

* cited by examiner

*Primary Examiner*—James M. Spear
(74) *Attorney, Agent, or Firm*—Banner & Witcoff, LTD

(57) ABSTRACT

This invention relates to coatings employed to coat medicinal tablets. Such tablets include but are not limited to small pellet(s) of medication to be taken orally. In particular this invention relates to the use of alginates and/or gellan gum, mixtures thereof and the like as tablet coatings. More in particular, this invention relates to the use of alginate and gellan gum as tablet coatings for tablets which are useful for humans including coating(s) on medicinal tablets and to a process for making such coatings.

6 Claims, No Drawings

ALGINATE AND GELLAN GUM AS TABLET COATING

This application claims the benefit of priority under 35 U.S.C. §119(e) of U.S. Provisional Application No. 60/064,454 filed Oct. 31, 1997.

BACKGROUND OF THE INVENTION

Field of the Invention

This invention relates to tablet coating compositions, tablet coatings and to a method to effectively prepare such composition(s). More particularly this invention relates to a tablet coating which comprises alginates and/or gellan gum for use on or with any tablet. Such tablets include but are not limited to a small pellet(s) of medication to be taken orally. Tablet coatings of this invention are useful for tablets for humans including coating(s) on medicinal tablets.

BACKGROUND OF THE INVENTION

Tablets are used in a variety of uses but of interest here are those tablets which are used to deliver a pharmacologically effective amount of a therapeutic drug to humans and animals. Typically such therapeutic effective drugs are those that possess and produce desirable drug effects after consumption by the human or animal.

In many medicinal uses, illustratively and without limitation, a coating is desired in order to obtain one of more of the following: appearance, identification, mouthfeel, reduce dust, stability, color, swallowability and stability, combinations thereof and the like.

Most tablet coatings today are made of low viscosity Hydroxypropylmethylcellulose (HPMC). Usually a ca. 10% HPMC solution, with appropriate plasticizer, is applied by a spraying system or device to a tablet. However, the industry has recognized the need for an improved tablet coating which would provide increased gloss and better mouthfeel for example.

Even with the foregoing and other tablet coating compositions of the art, the industry continues to desire a product which provides enhanced tablet coating properties. The art of preparing such a product economically and efficiently continues to be of interest to industry.

OBJECTS OF THE INVENTION

It is an object of this invention to provide an aqueous or adherent dry or substantially dry tablet coating composition for a tablet whereby such coating composition includes an alginate and/or a gellan gum or a mixture thereof.

It is another object of this invention to provide an efficient process for the preparing such a composition.

It is yet a further object of this invention to provide a highly useful tablet coating composition which provides enhanced properties to the tablet coated with such a composition.

It is yet another objective of this invention to provide a tablet coating system that provides improved recipient and patient mouthfeel.

These and other objectives are met in this invention which is hereinafter described in more detail.

BRIEF SUMMARY OF THE INVENTION

This invention comprises a method for effectively preparing aqueous and dry or substantially dry tablet coating compositions and a coated tablet, the tablet comprising a therapeutically effective amount of a consumable drug, wherein the adherent coating comprises alginate and/or gellan gum. The invention further comprises a coated tablet composition comprising an alginate and/or gellan gum and a method for preparing such a composition.

DETAILED DESCRIPTION OF THE INVENTION

Compositions which are useful as adherent coatings herein on tablets of any kind include those which contain alginates and/or gellan gum, mixtures thereof and the like.

Tablets useful herein come in all shapes and sizes. The tablet shape and size are not critical although preferred shapes and sizes are those which can be effectively consumed by a human or animal recipient with relative ease. Preferred tablets are medicinal tablets for humans or animals.

Gellan gum is useful herein and typical useful gellan gums are those naturally occurring polysaccharides that are typically produced by inoculating a carefully formulated fermentation medium with the microorganism Sphingamonas elodea (ATTC 31461). Gellan Gum is available in a clarified form (KELCOGEL7) for foods and industrial products and a clarified form of (GELRITE7) for microbiological media, plant tissue culture, and pharmaceutical applications. Gellan gum includes non-clarified, clarified, and partially-clarified native, deacetylated and partially deacetylated forms as well as mixtures thereof and the like.

Various alginates are useful in this invention include but are not limited to those which are described in detail by I. W. Cottrell and P. Kovacs in Alginates @ as Chapter 2 of Davidson, ea., Handbook of Water-Soluble Gums and Resins (1980) which is incorporated herein by reference in its entirety.

A particularly preferred alginate useful herein is a sodium alginate, a high-G, ultra low viscosity which is available from Monsanto Company, 800 North Lindbergh Blvd, St. Louis, Mo., 63167.

Other components of the coating composition of this invention include but are not limited to a plasticizer system and color additives as will be readily apparent to those of skill in the art. A typical plasticizer is glycerine although any equivalent or substantially equivalent plasticizer may be satisfactorily employed herein.

A typical composition of this invention comprises in the range from about 0.1% to about 3% alginate and gellan gum based on the dry weight of the tablet and preferably from about 0.5% to about 1% by weight alginate and gellan gum. When employed in such a combination, the weight ratio of alginate to gellan gum is in the range from about 1 to about 20 and preferably from about 1 to about 5 although greater and lesser ratios may be employed if desired as will be apparent to those of skill in the art after reading this specification.

Alginate and gellan gum may be individually employed as a tablet coating composition in this invention.

In practicing this invention, an aqueous composition comprising alginate and/or gellan gum is admixed in any suitable vessel prior to spraying the composition onto a tablet. Preferably, but not required, the alginate and/or gellan gum is admixed with water, the plasticizer is added thereto, and further mixing is carried out to form an aqueous tablet coating composition. The composition is mixed by any suitable mixing system preferably until complete or substantial mixing has been accomplished. A hot solution may be needed. Those of skill in the art will recognize that some heating will be necessary to achieve this.

As employed herein, the term "adherent" means that the coating adheres to the tablet until consumption whereupon the coating dissolves from the tablet containing a drug in order to enable release of the active ingredient therefrom. For example, the coating is wetted in the human's mouth, the recipient swallows the wetted coated tablet and the tablet coating dissolves in the human's stomach whereupon the tablet composition is made available to the patient or recipient to receive the medicinal value of the drug.

The aforementioned admixing is carried out by any convenient means including but not limited to use of a propeller or stirrer system although generally stirring by a convenient mechanical means is acceptable.

Application of the composition as a coating to the tablet is carried out by placing the tablets to receive a tablet composition of this invention in a spray tower such as fluid bed spray tower and then spraying the composition of this invention onto the tablets.

A typical spray tower includes but is not limited to a Wurster spray tower. Also, acceptable for use to prepare coating tablets of this invention are side vented coating pans and convention coating pans with spray nozzles. Also acceptable as a spray tower system is a conventional fluid bed tower with a suitable spray apparatus is included. Any spray system capable of applying a composition of this invention to a tablet is an acceptable system for coating tablets employing the aqueous coating composition of this invention. Any size spray system is acceptable. Batch and continuous processes, semi-continuous and variations thereof are envisioned without limitation.

Although the composition of this invention will initially be an aqueous composition, the tablet coating will become dry or substantially dry upon its exit from the spray system and on the surface of the coated tablet. In practice, coated tablets prepared herein are substantially dry or dry to the human touch. The coated tablets may be placed in suitable packaging.

The tablets include but are not limited to tablets of any convenient composition which may or not contain any pharmaceutically effective drug suitable for human and/or animal consumption. This coating may be employed on those tablets which do not contain any drug for use as placebos or blanks.

The amount of biologically active in any tablet will be a function of the ability of the composition of the tablet to load the active. This will vary depending on the choice of the biologically active ingredient and the components of the tablet as those of skill in the art will recognize.

The amount of coating provided to the surface of the tablet is an effective amount and it typically that amount which provides a minimum coverage of the exterior surface area of the tablet, although this invention also encompasses those instances where there is partial coverage of the exterior surface as well.

If desired one or more layers of coating may be employed using this invention. Those of skill in the art will be able to determine such depending on the drug, tablet size, physical and chemical and therapeutic properties and characteristics from a reading of this specification and using their skill in the art. The coating or coatings of this invention may be the initial exterior surface coating, an intermediate coating, a final coating or a combination. It is preferred that the layer of coating be continuous or nearly continuous and over the surface of the tablet. An effective depth of coating is provided. It is also desired that the tablet coatings herein be somewhat resilient with handling, resistant to peeling, flaking and being rubbed off the tablet.

EXAMPLES

Examples are provided by way of illustration and are not intended to limit the invention in any way. Alginates and Gellan gum were evaluated as an alternative to HPMC in tablet coatings. Various formulations were tested as shown in the Table following.

Low viscosity alginate solutions (about 10% alginate and about 2.5% gellan gum with about 25% weight plasticizer) were prepared as an aqueous solution and then successfully sprayed in a sprayer system onto tablets. These compositions provided acceptable glossy coatings with an optimum amount of plasticizer (glycerine) around 25% weight. A hot solution of Gelrite (2%, above 50° C.) was also successfully sprayed. Acceptable glossy coatings were obtained on tablets with much better mouth feel (less tacky) employing Gelrite.

Since most tablet coatings are presently made of low viscosity Hydroxypropylmethylcellulose (HPMC), this test compared alginates (Na-alginate and PGA) and gellan gum as inventive coating materials over similar processing conditions using HPMC representing the art. Several different formulations were prepared in a Wurster laboratory size spray column.

These compositions are summarized in Table 1. Sodium alginate: a high-G, ultra low viscosity Na-alginate: PGA (Propylene Glycol Alginate): Kelcoloid S (KDS) Gellan gum: Gelrite (deacetylated, clarified) HPMC: An ultra low viscosity sample was blended with Na-alginate (ratio 4/1).

Standard lactose tablets (350 mg), were used for this evaluation. All coating solutions were colored with various FDA certified dyes.

| ID# | Polymer Solution | Plasticizer (wt. % of polymer) | Sequestrant (wt. % of total solution) |
|---|---|---|---|
| 1 | Low viscosity alginate | 10% Glycerine | — |
| 2 | Low viscosity alginate | 25% Glycerine | — |
| 3 | 5% 80:20-Low viscosity alginate | 10% Glycerine | — |
| 4 | 5% 80:20-Low viscosity alginate:KDS | 20% Glycerine | — |
| 5 | 5% 50:50-Low viscosity alginate:HPMC | 12.5% Glycerine | |
| 6 | 2% GELRITE | 20% Glycerine | 0.1% Na-Citrate |
| 7 | 10% Low viscosity alginate | 25% Glycerine | — |
| 8 | 10% Low viscosity alginate | 25% Glycerine | 0.1% Na-Citrate |

Alginate solutions (5% and 10%), and the blends, were sprayed at room temperature using conventional techniques including controlling air flow, spray rate and temperature and the like.

The Gelrite solution was kept above 50° C. to avoid gelling in the spraying reservoir and the spray nozzle. The temperature of the tablets was approximately 60° C. in all runs (equating to compressed air inlet temperature).

All eight formulations were sprayable and produced acceptable tablet coatings with improved smoothness, uniformity, glossiness and non-tacky coating.

Pure low viscosity alginate solutions (5% and 10%) produced acceptable glossy films when the highest level of glycerine (20% and 25% respectively) was used as plasticizer. Some minor defects appeared when the lower level of plasticizer was employed.

Na-alginate coatings had a nicer appearance (more glossy) than conventional HPMC coatings. When placed in a human's mouth, the Na-alginate coating hydrated rapidly and formed a tacky layer on the surface of the tablet.

Using more constraining conditions (hot solution, 2% concentration), gellan gum was successfully sprayed as well. Nice glossy coatings were obtained with a more attractive mouth-feel. When put in a human mouth, these tablets became slippery and were not sticky.

Acceptable colored glossy coatings were obtained with pure A5B558 and Gelrite solutions using glycerine as a plasticizer.

It is preferred to apply gellan gum hot. The resulting product has an acceptable glossy film with a better mouth feel (less tacky). These are acceptable coatings and acceptable coated tablets.

Thus, it is apparent that there has been provided, in accordance with the instant invention, a process that fully satisfies the objects and advantages set forth herein above. While the invention has been described with respect to various specific examples and embodiments thereof, it is understood that the invention is not limited thereto and many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. A coated tablet comprising a tablet and at least one coating comprising alginate and gellan gum.
2. The coated tablet according to claim 1 wherein the alginate is sodium alginate.
3. The coated tablet according to claim 1 wherein the tablet comprises a drug.
4. The coated tablet according to claim 1 wherein the alginate and gellan gum comprise from about 0.1% to about 3% by weight based on the dry weight of the tablet.
5. The coated tablet according to claim 1 wherein the weight ratio of alginate to gellan gum is from about 1 to about 20.
6. The coated tablet according to claim 1 wherein the coating further comprises a plasticizer.

* * * * *